(12) United States Patent
Freeman et al.

(10) Patent No.: US 8,579,986 B1
(45) Date of Patent: Nov. 12, 2013

(54) BONE FUSION MATERIAL COMPRESSOR AND METHOD OF USE

(75) Inventors: Thomas B. Freeman, Tampa, FL (US); Wesley M. Johnson, Tampa, FL (US); Ben Guiot, Ottawa (CA)

(73) Assignee: University of South Florida, Tampa, FL (US)

( * ) Notice: Subject to any disclaimer, the term of this patent is extended or adjusted under 35 U.S.C. 154(b) by 1622 days.

(21) Appl. No.: 11/160,941

(22) Filed: Jul. 15, 2005

Related U.S. Application Data

(60) Provisional application No. 60/521,878, filed on Jul. 15, 2004.

(51) Int. Cl.
*A61F 2/28* (2006.01)

(52) U.S. Cl.
USPC ........................ 623/23.63; 623/923

(58) Field of Classification Search
USPC ................ 623/23.63, 23.61, 23.51, 923
See application file for complete search history.

(56) References Cited

U.S. PATENT DOCUMENTS

| | | | | |
|---|---|---|---|---|
| 5,009,905 | A * | 4/1991 | Ikeda | 426/297 |
| 6,719,795 | B1 * | 4/2004 | Cornwall et al. | 623/17.11 |
| 2003/0130744 | A1 * | 7/2003 | Bonutti | 623/23.63 |
| 2004/0249463 | A1 * | 12/2004 | Bindseil et al. | 623/17.16 |

* cited by examiner

*Primary Examiner* — Bruce E Snow
(74) *Attorney, Agent, or Firm* — Robert J. Varkonyi; Molly Sauter; Smith & Hopen, P.A.

(57) ABSTRACT

The present invention provides an apparatus and method that will allow surgeons to produce bone growth masses for use in spinal surgery that are capable of maintaining their physical integrity during placement and during the acute post operative period.

15 Claims, 7 Drawing Sheets

BONE FUSION MATERIAL COMPRESSOR AND METHOD OF USE

CROSS REFERENCE TO RELATED APPLICATIONS

This application claims priority to currently pending U.S. Provisional Patent Application No. 60/521,878, entitled, "Bone Fusion Material Compressor", filed Jul. 15, 2004.

BACKGROUND OF INVENTION

When performing spine surgery for the purpose of fusing segments together, a common practice known in the art is to obtain trabecular bone pieces from the iliac crest and position these pieces along the transverse processes of the spine posteriorly. Frequently, the surgeon will squeeze the trabecular pieces to form an approximately cylindrical mass, herein after called "mass" or "masses". However, the mass frequently falls apart when being placed in the desired location.

Accordingly, what is needed in the art is an apparatus and method that will allow surgeons to produce masses, in the operating room, that are capable of maintaining their physical integrity during placement and during the acute post operative period.

However, in view of the prior art considered as a whole at the time the present invention was made, it was not obvious to those of ordinary skill in this field that the identified improvements should be made nor would it have been obvious as to how to make the improvements if the need for such improvements had been perceived.

SUMMARY OF INVENTION

The longstanding but heretofore unfulfilled need for an apparatus and method that will allow surgeons or other operating room personnel to produce masses, in the operating room, that are capable of maintaining their physical integrity during placement and during the acute post operative period, is now met by a new, useful, and non-obvious invention.

In accordance with the present invention is provided an apparatus and method to prepare an approximately cylindrical mass of bone fusion and filing materials.

In a particular embodiment, a method for producing a non-structural surgical bone growth mass is provided. The method includes the steps of positioning at least one bone growth constituent within a substantially cylindrical element, tamping the at least one bone growth constituent into the cylindrical element to form a bone growth mass and extruding the bone growth mass from the cylindrical element for use in a surgical procedure.

Various devices are within the scope of the present invention for use in tamping the bone growth constituents within the cylindrical. In a particular embodiment, the tamping is accomplished through the use of a tamping rod element having dimensions corresponding to the interior dimension of the cylindrical element.

The bone growth constituents used to produce the bone growth mass in accordance with the present invention may be allograft, autograft, xenograft, aspirated bone marrow, osteoconductive substances, osteoinductive substances, synthetic bone growth products, or a combination of these constituents. The constituents may be introduced individually into the cylindrical element or combined into a mixture prior to being positioned within the cylindrical element.

To provide additional structure and stability to the bone growth mass, the mass may additionally be wrapped with a support wrapper. The wrapper may be bioresorbable or removed after the bone growth mass is in position.

In addition to forming a non-structural surgical bone growth mass utilizing a cylindrical element and tamping methodology, a structural surgical bone growth mass may also be formed utilizing an articulating sheet in accordance with the present invention. With this method, the bone growth constituents are positioned adjacent to the articulating sheet and a plurality of structural struts are positioned adjacent to the articulating sheet. The sheet is then rolled by hand to compress the constituents to surround the structural struts and to form a substantially cylindrical structural bone growth mass for use in a surgical procedure.

The bone growth constituents used to produce the structural bone growth mass in accordance with the present invention utilizing the articulating sheet may be allograft, autograft, xenograft, aspirated bone marrow, osteoconductive substances, osteoinductive substances, synthetic bone growth products, or a combination of these constituents. The constituents may be introduced individually or combined into a mixture prior to being positioned adjacent to the articulating sheet. The structural components may be bioresorbable and may be initially load bearing or capable of load bearing post implantation.

To provide additional structure and stability to the bone growth mass, the mass formed by the articulating sheet may additionally be wrapped with a support wrapper. The wrapper may be bioresorbable or removed after the bone growth mass is in position.

In a specific embodiment, a non-structural surgical bone growth mass preparation kit is provided for use by surgeons or other surgical personnel, the kit includes a substantially cylindrical element having at least one open end, the substantially cylindrical element dimensioned to resemble a desired surgical bone growth mass and a tamping element dimensioned to be positionable within the at least one open end of the cylindrical element. A plurality of cylinder and tamping rod dimensions are within the scope of the present invention.

In an additional embodiment, a structural surgical bone growth mass preparation kit for use by surgeons or other surgical personnel includes, an articulating sheet dimensioned to resemble a desired surgical bone growth mass, the articulating sheet further comprising a plurality of substantially inflexible rods positioned substantially parallel to each other and connected to each other to provide flexibility between the substantially inflexible rods. The rods may be hollow or solid and made from a variety of materials as are known in the art to be substantially inflexible along the longitudinal axis. This kit may additionally include bioresorbable structural components and load bearing components to incorporate into the bone growth mass constituent materials obtained either from the patient or other sources.

In yet another embodiment, a non-structural bone growth mass may be prepared using the articulating sheet by eliminating the structural struts and using only bone growth constituent materials as described.

While the detailed description of the embodiments is directed to an apparatus and method intended to be applicable to the spine, it is within the scope of the invention to utilize the apparatus and method described on all other areas of the human or other vertebrate body.

The present invention allows surgeons to combine bone growth material into forms that will hold-up when placed in the appropriate location. Current methods do not provide such an ability which results in bone growth material migration away from the very area for which is was intended.

DETAILED DESCRIPTION OF THE INVENTION

The invention consists of means and methods for a surgeon to prepare an approximately cylindrical mass of bone fusion and filling materials. The constituents can be a multiplicity of materials, including but not limited to: allograft, autograft, xenograft, aspirated bone marrow, osteoconductive substances, osteoinductive substances, and synthetic products. The approximately cylindrical may be of a structural or non-structural form. The methods used to compress the mass vary according to the constituents.

Figure 1:
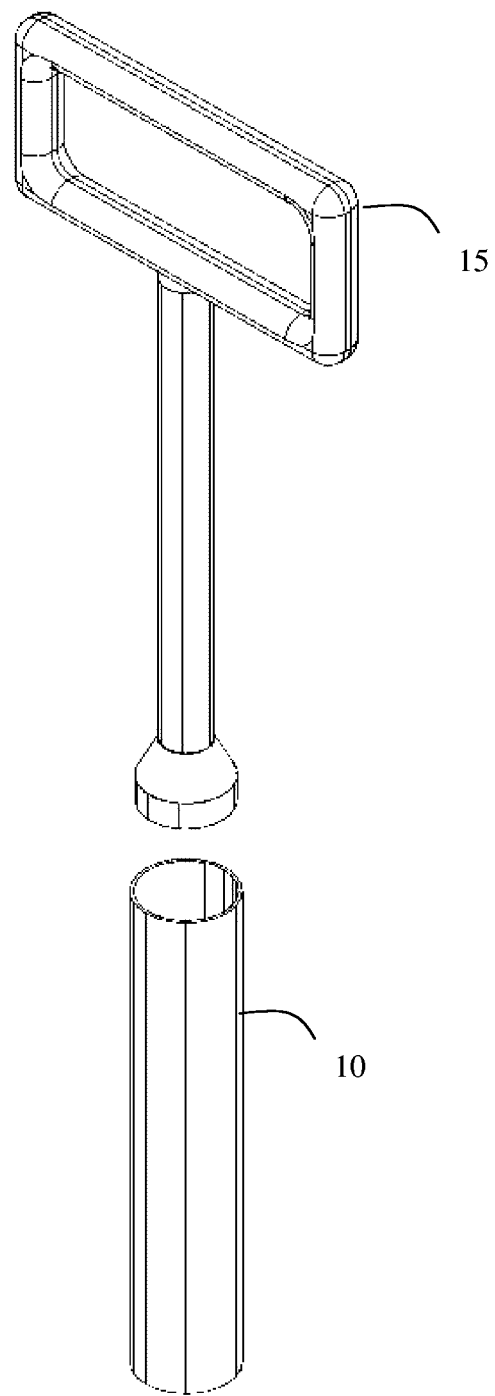
FIG. 1 is a diagrammatic view of the cylindrical element and tamping rod in accordance with the present invention.
Figure 2:
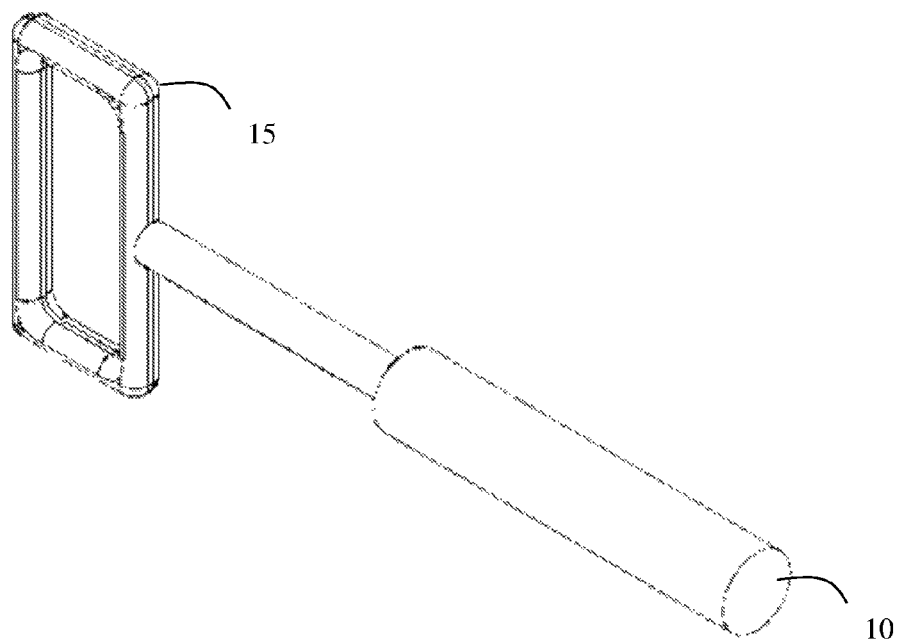
FIG. 2 is a diagrammatic view of the formation of the non-structural bone growth mass utilizing the cylindrical element in accordance with the present invention.
Figure 3A:
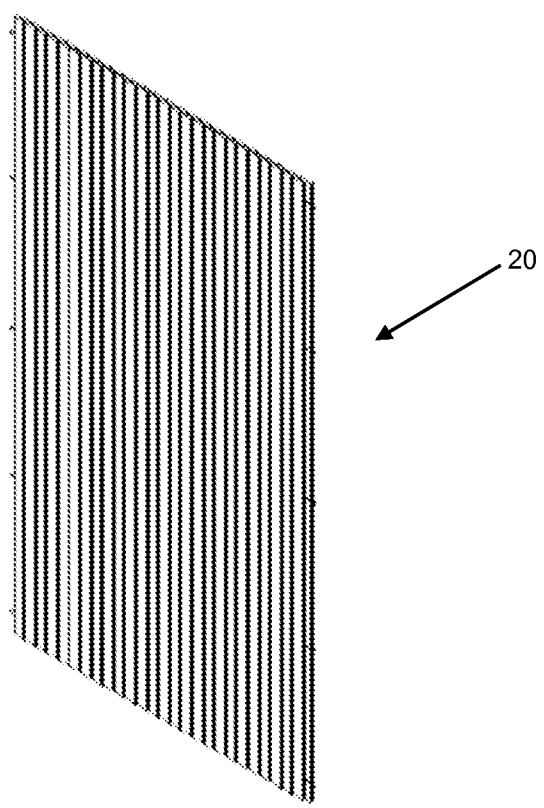
FIG. 3(A) is a diagrammatic view of the articulating sheet in accordance with the present invention when in an open position.
Figure 3B:
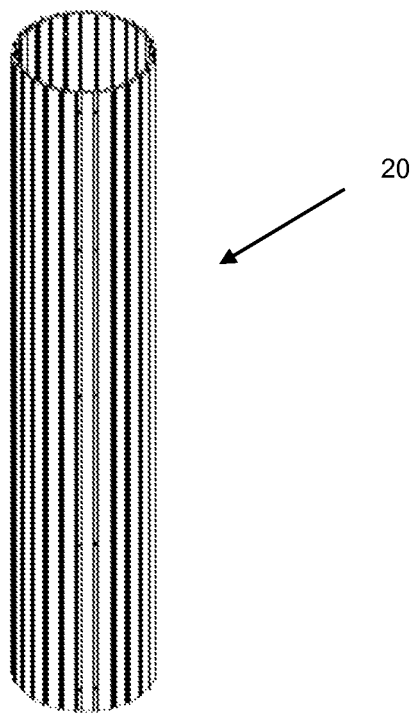
FIG. 3(B) is a diagrammatic view of the articulating sheet in accordance with the present when in a rolled position.

In a preferred embodiment of a non-structural form of the invention the constituents are: aspirated autologous bone marrow and or osteoinductive and osteoconductive substances, allograft putty, and synthetic bone chips. With reference to FIG. 1 and FIG. 2, the constituents are mixed in appropriate proportions and placed in a tamping device. The device consists of an open ended cylinder 10 with a multiplicity of cylinder diameters and a tamping rod 15. The tamping rod 15 is used to compress the constituents into a mass. The mass is then extruded from the end of the cylinder 10 and placed in a location prepared for it or for further processing. Further processing can consist of placing the tamped mass on a wrapper or on an articulating sheet similar to that described below.

In a particular embodiment for a structural bone growth mass, in addition to the bone growth constituents, the mass would additionally contain struts either initially capable of carrying load or acquiring load carrying capability over post implantation times on the order of days, as shown with reference to FIG. 3 through FIG. 6.

Figure 4:
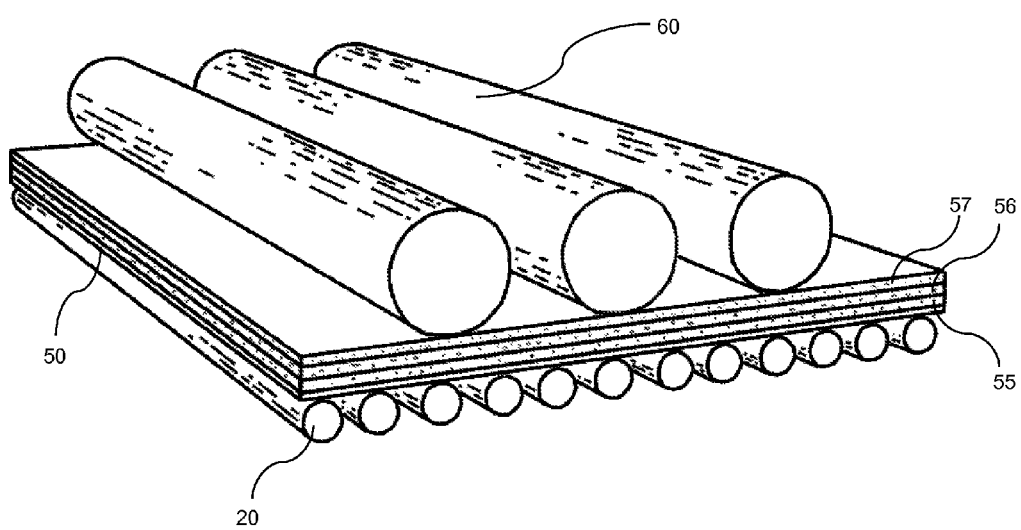
FIG. 4 is an isometric view of a structural bone growth mass formed utilizing the articulating sheet in accordance with the present invention.

For structural masses several alternating layers of material are arranged on an articulating sheet. The articulating sheet is shown with reference to FIG. 3(A). The articulating sheet 20 is a series of rods 25, hollow or solid, connected together in such a way as to allow flexibility along a plane described by the rod's 25 long axes but does not allow flexibility across the rods as in bending. In one preferred embodiment of a structural form of the invention the constituents are wrapper 50, aspirated autologous bone marrow 55, allograft putty 56, synthetic bone chips 57, and bioresorbable struts 60, as seen in FIG. 4. With this method, the articulating is effecting in apply the necessary compression to form the mass. The articulating sheet 20 is rolled by hand pressure to form the mass. The mass is then placed in a space provided for it.

Figure 5:
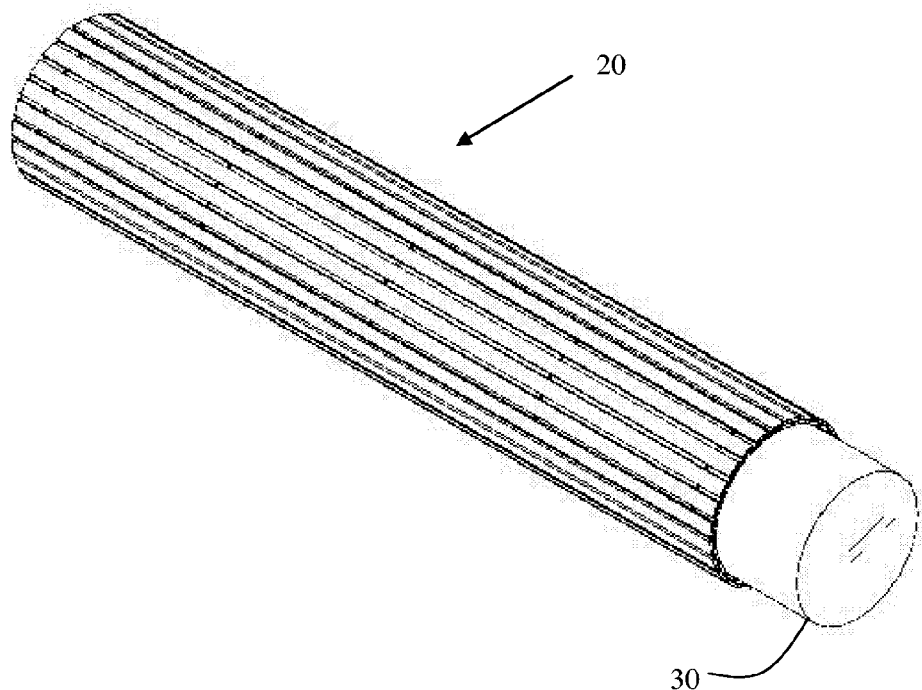
FIG. 5 is a diagrammatic view of a non-structural bone growth mass formed utilizing the articulating sheet in accordance with the present invention.

FIG. 5 illustrates a non-structural bone growth mass formed utilizing the articulating sheet 20 in accordance with the present invention. As shown, the articulating sheet 20 is used to compress and form the bone growth constituents 30 into the desired cylindrical mass.

Figure 6:
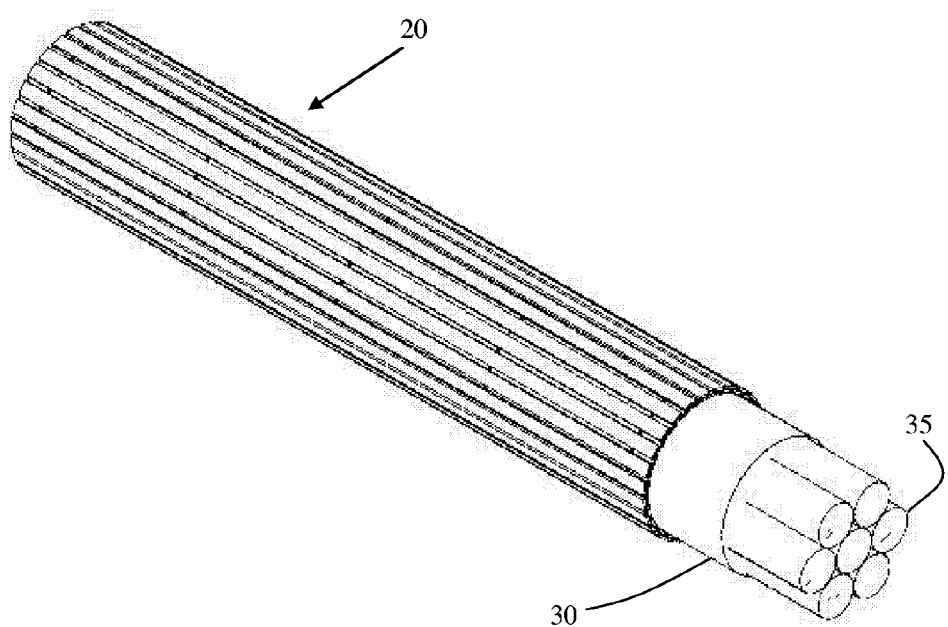
FIG. 6 is a diagrammatic view of a structural bone growth mass formed utilizing the articulating sheet in accordance with the present invention.

FIG. 6 illustrates a structural bone growth mass formed utilizing the articulating sheet 20 in accordance with the present invention. As shown, the articulating sheet 20 is used to compress and form the bone growth constituents 30 and the structural elements 35 into the desired cylindrical mass.

The methods and apparatus presented further include the capability of being sterilized utilizing heat, chemical, radiation, or other forms of sterilization known in the art.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A surgical bone growth mass preparation kit, the kit comprising:
   an articulating sheet dimensioned to resemble a desired surgical bone growth mass, the articulating sheet further comprising a plurality of substantially inflexible rods positioned substantially parallel to each other and connected to each other to provide flexibility between the substantially inflexible rods;
   at least one bone growth mass constituent, selected from the group consisting of autologous bone marrow, allograft putty, synthetic bone chips, bioresorbable struts, and osteoinductive and osteoconductive substances;
   a plurality of bioresorbable structural components positionable adjacent to the articulating sheet
   a tamping element, wherein the tamping element further comprises:
      a cylindrical member having at least one open end and a diameter dimensioned to accept the articulating sheet dimensioned to resemble a desired surgical bone growth mass and the at least one bone growth mass constituent;
      a tamping rod, wherein the tamping rod further comprises:
         a tamping member having a tamping face and a connection face, and dimensioned to engage the internal diameter of the cylindrical member;
         a connecting rod having a first end and a second end, wherein the first end is disposed on the connection face of the tamping member;
         a handle disposed on the second end of the connecting rod.

2. The surgical bone growth mass preparation kit of claim 1 further comprising a plurality of load bearing components positionable adjacent to the articulating sheet.

3. The surgical bone growth mass preparation kit of claim 1 further comprising a plurality of struts positionable adjacent to the articulating sheet.

4. The surgical bone growth mass preparation kit of claim 1 further comprising a support wrapper adapted to substantially surround the surgical bone growth mass.

5. The surgical bone growth mass preparation kit of claim 1 wherein the substantially inflexible rods are hollow or solid.

6. A surgical bone growth mass preparation kit, the kit comprising:
   an articulating sheet dimensioned to resemble a desired surgical bone growth mass, the articulating sheet further comprising a plurality of substantially inflexible rods positioned substantially parallel to each other and connected to each other to provide flexibility between the substantially inflexible rods;
   at least one bone growth mass constituent, selected from the group consisting of autologous bone marrow, allograft putty, synthetic bone chips, bioresorbable struts, and osteoinductive and osteoconductive substances;
      wherein the at least one bone growth mass constituent is circumscribed by the articulating sheet; and
   a tamping element, wherein the tamping element further comprises
      a cylindrical member having at least one open end and a diameter dimensioned to accept the articulating sheet dimensioned to resemble a desired surgical bone growth mass and the at least one bone growth mass constituent;
      a tamping rod, wherein the tamping rod further comprises:
         a tamping member having a tamping face and a connection face, and dimensioned to engage the internal diameter of the cylindrical member;
         a connecting rod having a first end and a second end, wherein the first end is disposed on the connection face of the tamping member;
         a handle disposed on the second end of the connecting rod.

7. The surgical bone growth mass preparation kit of claim 6 further comprising a plurality of load bearing components positionable adjacent to the articulating sheet.

8. The surgical bone growth mass preparation kit of claim 6 further comprising a plurality of struts positionable adjacent to the articulating sheet.

9. The surgical bone growth mass preparation kit of claim 6 further comprising a support wrapper adapted to substantially surround the surgical bone growth mass.

10. A method for producing a non-structural surgical bone growth mass, the method comprising the steps of:
    providing a surgical bone growth mass preparation kit, the kit comprising:
       an articulating sheet dimensioned to resemble a desired surgical bone growth mass, the articulating sheet further comprising a plurality of substantially inflexible rods positioned substantially parallel to each other and connected to each other to provide flexibility between the substantially inflexible rods;
       at least one bone growth mass constituent, selected from the group consisting of autologous bone marrow, allograft putty, synthetic bone chips, bioresorbable struts, and osteoinductive and osteoconductive substances;
          wherein the at least one bone growth mass constituent is circumscribed by the articulating sheet;
       a tamping element, wherein the tamping element further comprises
          a cylindrical member having at least one open end and a diameter dimensioned to accept the articulating sheet dimensioned to resemble a desired surgical bone growth mass and the at least one bone growth mass constituent;
          a tamping rod, wherein the tamping rod further comprises:
             a tamping member having a tamping face and a connection face, and dimensioned to engage the internal diameter of the cylindrical member;
             a connecting rod having a first end and a second end, wherein the first end is disposed on the connection face of the tamping member;
             a handle disposed on the second end of the connecting rod;
    positioning the at least one bone growth constituent within the tamping element;
    tamping the at least one bone growth constituent into the tamping element to form a non-structural bone growth mass; and
    extruding the bone growth mass from the tamping element for use in a surgical procedure.

11. The method of claim 10, wherein the step of tamping further comprises positioning the tamping rod element within the tamping element.

12. The method of claim 10, further comprising the step of wrapping the bone growth mass with a support wrapper following the step of extruding the bone growth mass from the tamping element.

13. A method for producing a structural surgical bone growth mass, the method comprising the steps of:
    providing a surgical bone growth mass preparation kit, the kit comprising:
       an articulating sheet dimensioned to resemble a desired surgical bone growth mass, the articulating sheet further comprising a plurality of substantially inflexible rods positioned substantially parallel to each other and connected to each other to provide flexibility between the substantially inflexible rods;
       at least one bone growth mass constituent, selected from the group consisting of autologous bone marrow, allograft putty, synthetic bone chips, bioresorbable struts, and osteoinductive and osteoconductive substances;
          wherein the at least one bone growth mass constituent is circumscribed by the articulating sheet;
       a tamping element, wherein the tamping element further comprises
          a cylindrical member having at least one open end and a diameter dimensioned to accept the articulating sheet dimensioned to resemble a desired surgical bone growth mass and the at least one bone growth mass constituent;
          a tamping rod, wherein the tamping rod further comprises:
             a tamping member having a tamping face and a connection face, and dimensioned to engage the internal diameter of the cylindrical member;
             a connecting rod having a first end and a second end, wherein the first end is disposed on the connection face of the tamping member;
             a handle disposed on the second end of the connecting rod;
    positioning the at least one bone growth constituent adjacent to the articulating sheet
    wherein the at least one bone growth mass constituent is circumscribed by the articulating sheet; and rolling the articulating sheet to surround and compact the bone growth constituent to form a substantially cylindrical structural bone growth mass for use in a surgical procedure.

14. The method of claim 13, further comprising the step of positioning the plurality of structural components within the bone growth constituent and adjacent to the bone growth constituent.

15. The method of claim 13, further comprising the step of removing the bone growth mass from within the articulating sheet and wrapping the bone growth mass with a support wrapper.

* * * * *